United States Patent [19]

Langsdorf, Jr.

[11] 4,048,156
[45] Sept. 13, 1977

[54] CARBAMOYLPHOSPHONATES

[75] Inventor: William P. Langsdorf, Jr., Wilmington, Del.

[73] Assignee: E. I Du Pont de Nemours and Company, Wilmington, Del.

[21] Appl. No.: 723,332

[22] Filed: Sept. 14, 1976

Related U.S. Application Data

[60] Division of Ser. No. 553,423, Feb. 26, 1975, Pat. No. 3,997,544, which is a division of Ser. No. 283,769, Aug. 25, 1972, Pat. No. 3,846,512, which is a continuation-in-part of Ser. No. 85,221, Oct. 29, 1970, Pat. No. 3,819,353, which is a continuation-in-part of Ser. No. 803,962, March 3, 1969, abandoned, which is a continuation-in-part of Ser. No. 731,732, May 24, 1968, Pat. No. 3,627,507.

[51] Int. Cl.$^2$ .............................................. C07F 9/40

[52] U.S. Cl. .................... 260/239 A; 260/239 BF; 260/239 EP; 260/293.76; 260/293.86; 260/326.2; 260/429.9; 260/924; 260/943; 544/64; 544/157

[58] Field of Search ...... 260/239 A, 239 BF, 239 EP, 260/247.2 A, 429.9, 293.76, 293.86, 924, 943, 326.2

[56] References Cited

U.S. PATENT DOCUMENTS

| | | | |
|---|---|---|---|
| 2,909,558 | 10/1959 | Reetz | 260/943 X |
| 3,354,166 | 11/1967 | Garner | 260/239 A X |
| 3,361,784 | 1/1968 | Leu | 260/293.86 X |
| 3,712,936 | 1/1973 | Jelinek | 260/247.2 A X |
| 3,784,638 | 1/1974 | Lambert | 260/239 A X |

Primary Examiner—Henry R. Jiles
Assistant Examiner—Richard A. Schwartz

[57] ABSTRACT

This disclosure teaches a method for employing novel carbamoylphosphonates such as ammonium ethyl carbamoylphosphonate, ammonium isopropyl carbamoylphosphonate and ammonium allyl carbamoylphosphonate to regulate the growth rate of plants.

1 Claim, No Drawings

CARBAMOYLPHOSPHONATES sp

CROSS REFERENCE TO RELATED APPLICATIONS

This application is a division of application Ser. No. 553,423, filed Feb. 26, 1975, now U.S. Pat. No. 3,997,544, which is a division of application Ser. No. 283,769, filed Aug. 25, 1972, now U.S. Pat. No. 3,846,512, which is a continuation-in-part of application Ser. No. 85,221, filed Oct. 29, 1970, now U.S. Pat. No. 3,819,353, which is a continuation-in-part of my application Ser. No. 803,962, filed Mar. 3, 1969, now abandoned, which was in turn a continuation-in-part of my earlier application Ser. No. 731,732, filed May 24, 1968, now U.S. Pat. No. 3,627,507.

BACKGROUND OF THE INVENTION

This invention relates to the discovery that a selected group of novel carbamoylphosphonates can be used to regulate the growth rate of plants. More particularly, the compounds of this invention are useful for controlling the growth of woody vegetation.

Related compounds such as the dialkyl carbamoylphosphonates are disclosed in U.S. Pat. No. 3,005,010 as herbicides.

SUMMARY OF THE INVENTION

In summary, this invention relates to a novel group of carbamoylphosphonates, the method of using the carbamoylphosphonates to regulate the growth rate of plants and formulations containing carbamoylphosphonates which are useful to regulate the growth rate of plants.

More particularly, the carbamoylphosphonates of this invention are represented by the formula:

$$R_1-O-\overset{\overset{O}{\|}}{\underset{\underset{OM}{|}}{P}}-\overset{\overset{O}{\|}}{C}-N\overset{R_2}{\underset{R_3}{\diagdown}}$$

wherein:

$R_1$ is alkyl of 1 through 6 carbon atoms, chloroalkyl of 1 through 6 carbon atoms containing up to three chlorine atoms, bromoalkyl of 1 through 6 carbon atoms containing up to 3 bromine atoms, alkoxy alkyl of 3 through 7 carbon atoms, alkenyl of 2 through 6 carbon atoms, alkynyl of 3 through 4 carbon atoms, phenyl or benzyl;

$R_2$ is hydrogen or methyl;

$R_3$ is hydrogen, methyl, amino, methylamino, or dimethylamino;

$R_2$ and $R_3$ can be taken together to form a ring selected from $-(CH_2)_2-O-(CH_2)_2-$ or $-(CH_2)_n-$ where $n$ is 2–6;

M is selected from the group consisting of ammonium, hydrogen, sodium, lithium, potassium, calcium, magnesium, zinc, manganese, barium or $$\overset{R_6}{\underset{R_7}{\diagdown}}N\overset{R_8}{\underset{R_9}{\diagup}}$$

where $R_6$, $R_7$ and $R_8$ can be the same or different and each can be hydrogen, alkyl of 1 through 4 carbon atoms, or hydroxy alkyl of two through 4 carbon atoms; and $R_9$ is hydrogen, alkyl of one through twelve carbon atoms, allyl, benzyl, amino, methylamino, or dimethylamino; $R_6$ and $R_7$ can be taken together to form a ring that is $-(CH_2)_2-O-(CH_2)_2-$ or $-(CH_2)_n-$ where $n$ is 2–6 and $R_8$ and $R_9$ are H.

Preferred compounds of this invention include those compounds of formula (1) where $R_1$ is alkyl of one through four carbons or alkenyl of three through four carbons; R2 and R3 are each hydrogen; and M is ammonium, hydrogen, or alkali metal such as sodium, lithium or potassium.

The most preferred compounds of this invention are ammonium allyl carbamoylphosphonate, ammonium ethyl carbamoylphosphonate, and ammonium isopropyl carbamoylphosphonate.

Another aspect of this invention relates to the method for modifying the growth rate of plants which comprises applying an effective amount of a compound of formula (1) to a plant to effect modification of the growth rate of said plant. Specifically, the method of this invention results in retarding the growth rate of the treated plants.

Another aspect of this invention relates to formulations of compounds of formula (1) with suitable agricultural adjuvants and modifiers or with tree wound dressings.

DESCRIPTION OF THE INVENTION

This invention is founded on the discovery that the compounds of formula (1) are useful for modifying the growth rate of plants. In this regard, it has been noted that the compounds of this invention, as represented by formula (1), are particularly useful to retard the growth rate of plants without killing them. The compounds of this invention are particularly useful to retard the growth of woody plants. The compounds of this invention can, therefore, be applied in areas such as power line rights-of-way where low-growing and slow growing vegetation is especially desirable.

In addition to their value as plant growth retardants the compounds of this invention can also be used to control flowering, fruit set and coloration on apples and other fruits. They are useful to control the growth and flowering of ornamental species such as chrysanthemum and azalea.

The compounds of this invention can also be used to prolong the dormancy of perennial plants, and thereby protect the unsprouted buds from frost damage. This can be especially important in the protection of flower buds, which in some years, may sprout early and be killed by cold temperatures.

PREPARATION

The ammonium carbamoylphosphonate salts of this invention are readily prepared by the interaction of the diesters of carboalkoxyphosphonic acids with aqueous solutions of ammonia, primary amines or secondary amines.

The reaction can be considered to occur in two steps as is illustrated by the following equations.

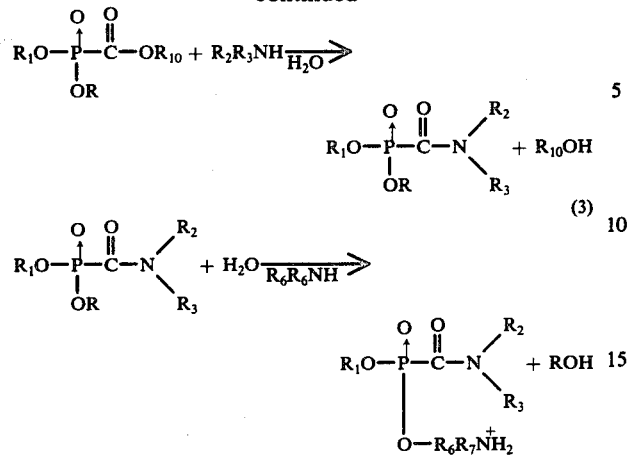

(3)

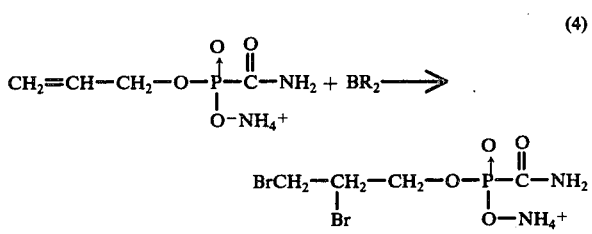

In equations (2) and (3) R is alkyl of 1 through 6 carbon atoms, chloroalkyl of 1 through 6 carbon atoms containing up to 3 chlorine atoms, bromoalkyl of one through 6 carbon atoms containing up to 3 bromine atoms, alkoxy alkyl of from 3 through 7 carbon atoms, alkenyl of 2 through 6 carbon atoms, alkynyl of 3 through 4 carbon atoms, phenyl or benzyl; $R_{10}$ is alkyl of 1 through 4 carbon atoms, preferably methyl or ethyl; $R_1$ is alkyl of 1 through 6 carbon atoms, chloroalkyl of 1 through 6 carbon atoms containing up to 3 chlorine atoms, bromoalkyl of 1 through 6 carbon atoms containing up to 3 bromine atoms, alkoxy alkyl of 3 through 7 carbon atoms, alkenyl of 2 through 6 carbon atoms, alkynyl of 3 through 4 carbon atoms, phenyl or benzyl; $R_2$ is hydrogen or methyl; $R_3$ is hydrogen, methyl, amino, methylamino, or dimethylamino; $R_2$ and $R_3$ can be taken together to form a ring selected from —$(CH_2)_2$—O—$(CH_2)_2$— or —$(CH_2)_n$— where $n$ is 2-6; M is selected from the group consisting of ammonium, hydrogen, sodium, lithium, potassium, calcium, magnesium, zinc, manganese, barium or

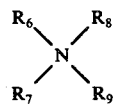

where $R_6$, $R_7$ and $R_8$ can be the same or different and each can be hydrogen, alkyl of 1 through 4 carbon atoms, or hydroxy alkyl of 2 through 4 carbon atoms; and $R_9$ is hydrogen, alkyl of 1 through 12 carbon atoms, allyl, benzyl, amino, methylamino, or dimethylamino; $R_6$ and $R_7$ can be taken together to form a ring that is —$(CH_2)_2$—O—$(CH_2)_2$— or —$(CH_2)_n$— where $n$ is 2-6 and $R_8$ and $R_9$ are H.

The synthesis method, exemplified by equations (2) and (3) involves concurrent or consecutive aminolysis and hydrolysis of the starting dialkyl carboalkoxyphosphonate by interaction with water and the amine reactant.

While equations (2) and (3) represent the route predominantly taken by the reaction when combined in one operation, some hydrolysis may occur during or before aminolysis. However, the postulated reaction as represented by equations (2) and (3) favoring formation of the carbamoylphosphonate intermediate is proved experimentally, as it is possible in some instances to isolate the carbamoylphosphonate intermediate shown as the product of equation (2). It has, of course, also been experimentally demonstrated that the product of equation (3) is in fact obtained.

An alternate method for synthesis of those compounds of this invention where $R_1$ is substituted by chlorine or bromine consists of the addition of halogen or hydrogen halide to the double bond of the compounds of this invention where $R_1$ is alkenyl. This reaction is illustrated by equation (4).

(4)

$$CH_2=CH-CH_2-O-\underset{\underset{O^-NH_4^+}{|}}{\overset{\overset{O}{\uparrow}}{P}}-\overset{\overset{O}{\|}}{C}-NH_2 + BR_2 \longrightarrow$$

$$BrCH_2-CH_2-CH_2-O-\underset{\underset{O-NH_4^+}{|}}{\overset{\overset{O}{\uparrow}}{P}}-\overset{\overset{O}{\|}}{C}-NH_2$$

The dialkyl carbamoylphosphonates prepared as described above or by methods described in the chemical literature are readily hydrolized to the monoester salt compounds of this invention by addition to aqueous ammonia or amine solutions. This procedure may be used therefore to obtain a "mixed" product, comprising a salt of one amine and an amide of another. This will be discussed and exemplified below.

The dialkyl carboalkoxyphosphonates and dialkyl carbamolyphosphonates used for the synthesis of the compounds of this invention can be prepared by methods available in the literature, such as Nylen, Chem. Ber. 57, 1023 (1924) and Reetz et al., J.A.C.S. 77, 3813-16 (1955) using appropriate ester intermediates. Generally, the alkoxy group of the carboalkoxyphosphonate is limited for practical purposes to methyl and ethyl, since there appears to be no advantage to increasing the size of the alcohol moiety. However, higher alcohol derivatives are useful in some instances.

The following are illustrative of typical diesters of the carboalkoxyphosphonates:
Diethyl carbomethoxyphosphonate
Diallyl carbomethoxyphosphonate
Diisopropyl carboethoxyphosphonate
Dibutyl carbobutoxyphosphonate
Dimethallyl carboethoxyphosphonate The following are illustrative of typical carbamoylphosphonate esters:
Diethyl carbamoylphosphonate
Diallyl N,N-dimethylcarbamoylphosphonate
Diallyl carbamoylphosphonate
Dipropyl N-methylcarbamoylphosphonate
Dimethyl piperidinocarbonylphosphonate The following are illustrative of the amines which can be used for the amination and/or hydrolysis of the esters:
Ammonia
Methylamine
Dimethylamine
Allylamine
Propylamine
Ethylamine
Morpholine
Piperidine
Methylhydrazine
N,N-Dimethylhydrazine
Ethanolamine More particularly, in the preferred procedure for preparing the ammonium alkyl carbamoylphosphonates of this invention, a dialkyl carboalkoxyphosphonate or dialkyl carbamoylphosphonate is added to a stirred aqueous solution of ammonia or other amine. Stirring is contained until a clear solution is obtained. The resultant salt can then be isolated by removal of the water through evaporation or by stripping under reduced pressure. In general, these salts are stable white crystalline solids or viscous liquids. Those which are solid can be recrystallized from one or a mixture of several lower alcohols. However, most of the products are suitable for use without purification.

It is preferred that an excess of ammonia or amine be employed in this reaction to insure good yields and rapid reaction. A ratio of diester to amine of 1 to 2 or greater is employed. Preferably the ratio of diester to amine of between 1 to 2 and 1 to 10 is employed. The excess amine insures that amidation of the carboxylic ester rather than hydrolysis is the predominant reaction.

It is also preferred that a concentration of ammonia or amine of from 25 to 50% be employed, although the reaction can be operated at higher or lower concentrations.

When the amine reactant is not highly soluble in water, another solvent, such as methanol or ethanol can be added to the aqueous system to solubilize the amine reactant and thereby increase its reactivity.

This process can conveniently be carried out at about room temperature, although higher temperatures can also be employed if it is desired to speed up the rate of reaction. This process is moderately exothermic, and therefore must be controlled by regulation of the diester addition rate and/or by external cooling to maintain the desired temperature.

A highly satisfactory procedure is to slowly add the diester to a stirring aqueous solution of the amine which is cooled and maintained at about 15° C. When addition of the diester is complete, the temperature of the mixture is allowed to come to room temperature or slightly above. Generally, the reaction is complete in a few minutes to several hours depending on the reactants and conditions used.

The ammonium salts prepared as described above can be converted to salts of other bases or of alkaline and alkaline earth metals by interchanging the ammonium salt with appropriate bases or salts.

Another method is to convert the ammonium salt to the free acid, and then neutralize the free acid with the appropriate base or salt.

The following illustrative examples are presented to further illustrate this invention. In the following examples, parts and percentages are by weight unless otherwise specified.

EXAMPLE 1

A solution of 48.5 parts of 29% aqueous ammonium hydroxide is stirred and cooled with an external ice bath to 15° C. To the cooled solution 22 parts of diallyl carbomethoxyphosphonate is slowly added over a ten-minute period. The mixture turns cloudy, but clears up after about 15 minutes. During this time, the mixture is allowed to warm spontaneously to about 30° C. and stirring is continued for two hours. The clear solution is stripped under reduced pressure (15 mm of Hg) at a water-bath temperature or 70° C. The residue is a white crystalline solid which is recrystallized from absolute ethyl alcohol, giving 12.3 parts of ammonium allyl carbamoylphosphonate, m.p. 160-162.5° C. Nonaqueous titration either as an acid or a base gives a molcular weight of 182±1.

EXAMPLE 2-19

The procedure of Example 1 is repeated by substituting an equivalent amount of the indicated "Phosphonate Ester" for the diallyl carbomethoxyphosphonate of Example 1 to produce the indicated "Salt Product."

| Ex. | Phosphonate Ester | Salt Product |
| --- | --- | --- |
| 2 | diethyl carbomethoxyphosphonate | ammonium ethyl carbamoylphosphonate, m.p. 173-176 |
| 3 | bis(2-chloroethyl)carbobutoxyphosphonate | ammonium 2-chloroethyl carbamoylphosphonate, m.p. 117-120 |
| 4 | dibutyl carboethoxyphosphonate | ammonium butyl carbamoylphosphonate m.p. 205.5-206.5 |
| 5 | diallyl carboethoxyphosphonate | ammonium allyl carbamoylphosphonate |
| 6 | dimethallyl carbomethoxyphosphonate | ammonium methallyl carbamoylphosphonate, m.p. 193-197 |
| 7 | diisopropyl carboethoxyphosphonate | ammonium isopropyl carbamoylphosphonate, m.p. 213-216 (dec.) |
| 8 | dimethyl carbomethoxyphosphonate | ammonium methyl carbamoylphosphonate, m.p. 148-151 |
| 9 | dipropyl carbopropoxyphosphonate | ammonium propyl carbomylphosphonate, m.p. 190-192 (dec.) |
| 10 | diisobutyl carbomethoxyphosphonate | ammonium isobutyl carbamoylphosphonate, m.p. 221-222 (dec.) |
| 11 | dihexyl carbomethoxyphosphonate | ammonium hexyl carbamoylphosphonate, m.p. 212 (dec.) |
| 12 | bis(1-ethyl-2-butenyl)carbomethoxyphosphonate | ammonium (1-ethyl-2-butenyl)carbamoylphosphonate |
| 13 | bis(2-methoxyethyl)carbomethoxyphosphonate | ammonium 2-methoxyethyl carbamoylphosphonate |
| 14 | bis(2-bromopropyl)carbomethoxyphosphonate | ammonium 2-bromopropyl carbamoylphosphonate |
| 15 | bis(6-chlorohexyl)carbomethoxyphosphonate | ammonium 6-chlorohexyl carbamoylphosphonate |
| 16 | bis(6-bromohexyl)carbomethoxyphosphonate | ammonium 6-bromohexyl carbamoylphosphonate |

-continued

| Ex. | Phosphonate Ester | Salt Product |
|---|---|---|
| 17 | bis(2-butoxyethyl)carbomethoxyphosphonate | ammonium 2-butoxyethyl carbamoylphosphonate, hygroscopic acid |
| 18 | bis(2,2,2-trichloroethyl)carbomethoxyphosphonate | ammonium 2,2,2-trichloroethylcarbamoylphosphonate |
| 19 | bis(2,2,2-tribromoethyl)carbomethoxyphosphonate | ammonium 2,2,2-tribromoethylcarbamoylphosphonate |

EXAMPLE 20

To a stirring ice-chilled solution of 35 parts 40% methylamine in water is added slowly 8.4 parts od dimethyl carbomethoxyphosphonate. The mixture is warmed to 25° C. and allowed to stir for 3 hours. The clear solution on stripping under reduced pressure yields 9.6 parts methylammonium methyl N-methylcarbamoylphosphonate as a colorless oil. The product analyzes for the dihydrate.

EXAMPLES 21-27

The procedure of Example 20 is repeated substituting an equivalent amount of the indicated "Aqueous Amine" for the methylamine of Example 20 and an equivalent amount of the indicated "Phosphonate Ester" for the dimethylcarbomethoxyphosphonate of Example 20 to obtain the indicated Salt Product. Most of the indicated Salt Products are isolated as liquids or low melting solids.

| Ex. | Aqueous Amine | Phosphonate Ester | Salt Product |
|---|---|---|---|
| 21 | methylamine (40%) | diethyl carboethoxyphosphonate | methylammonium ethyl N-methylcarbamoylphosphonate |
| 22 | methylamine (40%) | diisopropyl carbomethoxyphosphonate | methylammonium isopropyl N-methylcarbamoyl phosphonate |
| 23 | methylamine (40%) | diallyl carboethoxyphosphonate | methylammonium allyl N-methylcarbamoylphosphonate |
| 24 | dimethylamine (25%) | diethyl carbomethoxyphosphonate | dimethylammonium ethyl N,N-dimethylcarbamoyl phosphonate |
| 25 | methylhydrazine (50%) | diethyl carboethoxyphosphonate | methyl carbazoylphosphonic acid monoethyl ester salt with methylhydrazine |
| 26 | piperidine (50%) | dibenzyl carbomethoxyphosphonate | piperidinium benzyl piperidinocarbonylphosphonate |
| 27 | 1,1-dimethylhydrazine (35%) | dipropyl carbomethoxyphosphonate | 1,1-dimethyl hydrazinium propyl 3,3-dimethylcarbazoylphosphonate |

EXAMPLE 28

Eight parts of diethyl N-methylcarbamoylphosphonate is added slowly to 18 parts of a 29% aqueous solution of ammonia, while holding the temperature at 25° C. by external cooling. The unreacted ammonium hydroxide is allowed to evaporate, giving a white, crystalline, solid residue. Recrystallization from absolute ethanol gives 5 parts of ammonium ethyl N-methylcarbamoylphosphonate, m.p. 189° C.

EXAMPLES 29-41

The procedure of Example 28 is repeated substituting an equivalent amount of the indicated Aqueous Amine for the ammonia of Example 28 and an equivalent amount of the indicated Phosphonate Ester for the diethyl methylcarbamoylphosphonate of Example 28 to obtain the indicated Salt Product.

| Ex. | Aqueous Amine | Phosphonate Ester | Salt Product |
|---|---|---|---|
| 29 | ammonia (20%) | diphenyl N-methyl carbamoylphosphonate | ammonium phenyl N-methyl carbamoylphosphonate |
| 30 | methylamine (25%) | dimethyl N,N-dimethyl carbamoylphosphonate | methylammonium methyl N,N-dimethylcarbamoylphosphonate |
| 31 | dimethylamine (25%) | diethyl carbamoylphosphonate | dimethylammonium ethyl carbamoylphosphonate |
| 32 | allylamine (25%) | diallyl carbamoylphosphonate | allylammonium allyl carbamoylphosphonate |
| 33 | isobutylamine (20%) | diisopropyl N-methyl carbamoylphosphonate | isobutylammonium isopropyl N- |

-continued

| Ex. | Aqueous Amine | Phosphonate Ester | Salt Product |
|---|---|---|---|
| 34 | methylamine (20%) | diisopropyl morpholino-carbonylphosphonate | methylcarbamoylphosphonate methylammonium isopropyl morpholinocarbonylphosphonate |
| 35 | triethanolamine | diallyl carbamoyl-phosphonate | triethanol-ammonium allyl carbamoylphosphonate |
| 36 | ammonia (29%) | diethyl pyrrolidino-carbonylphosphonate | ammonium ethyl pyrrolidinocarbamoylphosphonate, m.p. 189–192 (dec.) |
| 37 | ammonia (29%) | diethyl morpholino-carbonylphosphonate | ammonium ethyl morpholinocarbonylphosphonate, m.p. 183–185 (dec.) |
| 38 | ammonia (29%) | diethyl N,N-dimethyl-carbamoylphosphonate | ammonium ethyl N,N-dimethylcarbamoylphosphonate, m.p. 140.5–142.5 |
| 39 | ammonia (29%) | bis(3-butynyl)N,N-dimethylcarbamoyl-phosphonate | ammonium 3-butynyl N,N-dimethylcarbamoylphosphonate |
| 40 | ammonia (29%) | diethyl N-methylcar-bamoylphosphonate | ammonium ethyl N-methylcarbamoyl-phosphonate |
| 41 | ammonia | diethyl aziridinium-carbamoylphosphonate | ammonium ethyl aziridiniumcarbamoylphosphonate |

EXAMPLE 42

To a mixture of 12.1 parts of ammonium allylcarbamoylphosphonate and 100 parts of ethanol is added dropwise 8 parts of bromine. The reaction mixture is filtered giving 8.5 parts of ammonium 2,3-dibromopropyl carbamoylphosphonate, m.p. 175–177° C.

EXAMPLES 43–44

The procedure of Example 42 is repeated substituting an equivalent amount of the indicated "Alkenyl Reagent" for the ammonium allylcarbamoylphosphonate of Example 42 and an equivalent amount of the indicated "Halogen" for the bromine of Example 42 to obtain the indicated "Product".

| 43 | ammonium methallyl carbamoylphosphonate | chlorine | ammonium 2,3-dichloro-2-methylpropyl carbamoylphosphonate |
|---|---|---|---|
| 44 | ammonium but-2-enyl carbamoylphosphonate | bromine | ammonium 2,3-dibromobutyl carbamoylphosphonate |

EXAMPLE 45

An aqueous solution of 45 parts ammonium hydroxide is stirred and chilled with an ice bath, while 24.4 parts benzyl methyl carbomethoxyphosphonate is added slowly. Stirring is continued until a clear solution is obtained. Unreacted ammonium hydroxide and water are removed from the mixture under reduced pressure, leaving as a solid residue ammonium monobenzyl carbamoylphosphonate, m.p. 186, after recrystallization from ethanol.

EXAMPLES 46–51

The procedure of Example 45 is repeated substituting an equivalent amount of the indicated Aqueous Amine for the ammonium hydroxide of Example 45 and an equivalent amount of the indicated Phosphonate Ester for the benzyl methyl carbomethoxyphosphonate of Example 45 to obtain the indicated Salt Product as a principal product of this procedure.

| Ex. | Aqueous Amine | Phosphonate Ester | Salt Product |
|---|---|---|---|
| 46 | methylamine (40%) | benzyl methyl carbomethoxy-phosphonate | methylammonium benzyl N-methyl-carbamoylphosphonate |
| 47 | ammonia (29%) | methyl phenyl carbomethoxy-phosphonate | ammonium phenyl car-bamoylphosphonate, m.p. 197–199 (dec.) |
| 48 | dimethylamine (25%) | butyl ether carbomethoxy-phosphonate | dimethylammonium butyl N,N-dimethyl-carbamoylphosphonate |
| 49 | ethylamine (50%) | methyl propargyl carbomethoxy-phosphonate | ethylammonium propargyl N-ethylcarbamoyl-phosphonate |
| 50 | allylamine (25%) | methyl allyl carboethoxy-phosphonate | allylammonium allyl N-allyl carbamoylphosphonate |
| 51 | pyrrolidine (30%) | methyl propyl carbomethoxy-phosphonate | pyrrolidinium propyl pyrrolidinecarbonyl-phosphonate |

EXAMPLE 52

To a stirring suspension of 21.2 parts ammonium butyl N-methylcarbamoylphosphonate and 100 parts methanol is added 42 parts of a 40% solution of N-benzyltrimethylammonium hydroxide in methanol. Ammonia and methanol are stripped from the mixture at 40° C. under reduced pressure, leaving benzyltrimethylammonium butyl N-methylcarbomoylphosphonate as a residue.

EXAMPLES 53–56

The procedure of Example 52 is repeated substituting an equivalent amount of the indicated "Base" for the N-benzyltrimethylamonium hydroxide of Example 52 and an equivalent amount of the indicated Ammonium Phosphonate for the ammonium butyl N-methylcarbamoylphosphonate of Example 52 to obtain the indicated Salt Product.

| Ex. | Base | Ammonium Phosphonate | Salt Product |
|---|---|---|---|
| 53 | tetraethylammonium hydroxide | ammonium allyl carbamoylphosphonate | tetraethylammonium monoallyl carbamoylphosphonate |
| 54 | trimethylamine (large excess) | ammonium ethyl N-methylcarbamoylphosphonate | trimethylammonium monoethyl N-methyl carbamoylphosphonate |
| 55 | ethanolamine | ammonium methallyl hexahydroazepinocarbonylphosphonate | ethanolammonium methyallyl hexahydroazepinocarbonylphosphonate |
| 56 | benzylamine | ethylammonium isopropyl carbamoylphosphonate | benzylammonium isopropyl carbamoyl phosphonate |

EXAMPLE 57

A 5% aqueous solution of ammonium ethyl carbamoylphosphonate is passed through a packed column of sulfonated polystyrene copolymer hydrogen-type resin to convert the salt to the free acid. Evaporation of the water gives a residue of the acid ester, ethyl carbamoylphosphonic acid, m.p. 130° C.

EXAMPLES 58–60

The procedure of Example 57 is repeated, first obtaining the indicated "Acid Ester" in aqueous solution and then removing the water to obtain the water-free product, usually a solid.

| Ex. | Ammonium Phosphonate | Acid Ester |
|---|---|---|
| 58 | ammonium methyl N-methylcarbonylphosphonate | methyl N-methylcarbamoylphosphonic acid |
| 59 | ammonium isopropyl carbamoylphosphonate | isopropyl carbamoylphosphonic acid |
| 60 | ammonium alkyl carbamoylphosphonate | alkyl carbamoylphosphonic acid |

EXAMPLE 61

A 5% aqueous solution of ammonium propyl N-methylcarbamoylphosphonate is passed through a packed column of sulfonated polystyrene copolymer type resin to convert the salt to the free acid. This is neutralized with the equivalent amount of sodium bicarbonate to give a solution of essentially pure sodium propyl N-methylcarbamoylphosphonate. Evaporation of this solution gives the solid salt product.

EXAMPLES 62–75

The procedure of Example 61 is repeated, first obtaining the free acids of the indicated Ammonium Phosphonate as was done in Example 61 and then neutralizing the acid with the indicated Base according to the procedure of Example 61 to obtain the indicated Salt Product.

| Ex. | Ammonium Phosphonate | Base | Salt Product |
|---|---|---|---|
| 62 | ammonium phenyl carbamoylphosphonate | sodium bicarbonate | sodium phenyl carbamoylphosphonate |
| 63 | ammonium benzyl carbamoylphosphonate | calcium hydroxide | hemicalcium benzyl carbamoylphosphonate |
| 64 | ammonium ethyl carbamoylphosphonate | barium hydroxide | hemibarium ethyl carbamoylphosphonate |
| 65 | ammonium methyl-N,N-dimethylcarbamoyl phosphonate | hydroxyethyltrimethylammonium hydroxide | hydroxyethyltrimethylammonium methyl N,N-dimethyl carbamoylphosphonate |
| 66 | ammonium benzyl carbamoylphosphonate | benzyltrimethylammonium hydroxide | benzyltrimethylammonium benzyl carbamoylphosphonate |
| 67 | ammonium allyl carbamoylphosphonate | magnesium hydroxide | hemimagnesium allyl carbamoylphosphonate |
| 68 | ammonium butyl N-methyl carbamoylphosphonate | morpholine | morpholinium butyl N-methylcarbamoylphosphonate |
| 69 | ammonium mono-isopropyl morpholino-carbonyl-phosphonate | trimethylamine | trimethylammonium isopropyl morpholinocarbonylphosphonate |
| 70 | ammonium ethyl carbamoylphosphonate | tetrabutylammonium hydroxide | tetrabutylammonium ethyl carbamoylphosphonate, hygroscopic solid |
| 71 | ammonium ethyl carbamoylphosphonate | lithium carbonate | lithium ethyl carbamoylphosphonate, m.p. above 300° C. |
| 72 | ammonium ethyl carbamoylphosphonate | zinc carbonate | hemizinc ethyl carbamoylphosphonate, m.p. 244 (dec.) |
| 73 | ammonium isopropyl carbamoylphosphonate | dodecylamine | dodecylammonium isopropyl carbamoyl phosphonate |
| 74 | ammonium allyl carbamoylphosphonate | manganous carbonate | hemimanganous allyl carbamoylphosphonate |
| 75 | ammonium butyl morpholinumcarbonylphosphonate | dodecyltrimethyl ammonium hydroxide | dodecyltrimethylammonium butyl morpholiniumcarbony phosphonate |

EXAMPLE 76

To a stirred solution of 10 parts of potassium bicarbonate and 50 parts of water is added 18.4 parts ammonium isobutyl carbamoylphosphonate. Stirring is continued until solution is complete. The solution is evaporated to dryness, giving the solid product, potassium isobutylcarbamoylphosphonate.

EXAMPLES 77-80

The procedure of Example 76 is repeated substituting the indicated "Bicarbonate Salt" for the potassium bicarbonate of Example 76 and an equivalent amount of the indicated "Carbamoylphosphonate" for the ammonium monoisobutyl carbamoylphosphonate of Example 76 to obtain the indicated Salt Product.

| Ex. | Bicarbonate Salt | Carbamoyl-phosphonate | Salt Product |
|---|---|---|---|
| 77 | sodium bicarbonate | ammonium ethyl N-methylcarbamoyl-phosphonate | sodium ethyl N-methylcarbamoyl-phosphonate |
| 78 | potassium bicarbonate | ammonium benzyl carbamoylphosphonate | potassium benzyl carbamoylphosphonate |
| 79 | tetramethyl-ammonium bicarbonate | ammonium mono-allyl piperidino-carbonylphosphonate | tetramethylammonium allyl piperidino-carbonylphosphonate |
| 80 | benzyltri-methyl-ammonium bicarbonate | ammonium butyl carbamoylphosphonate | benzyltri-methylammonium butyl carbamoylphosphonate |

Formulation

Plant growth modifying compositions of the present invention can be prepared by admixing at least one of the compounds of this invention with pest control adjuvants or modifiers ot provide compositions in the form of dusts, water-soluble powders, solutions, granules or pellets. In addition, the plant growth modifying agents such as maleic hydrazide and "Alar" (N-dimethylaminosuccinamic acid) can be included in the compositions of this invention in combination with the compounds of this invention.

Compositions of the invention, may contain as a conditioning agent one or more surface-active agents, sometimes called surfactants, in amounts sufficient to render a given composition containing the compounds of this invention readily soluble in water or capable of wetting foliage efficiently.

The surface-active agent used in this invention can be a wetting, dispersing or an emulsifying agent which will assist dispersion and solution of the active compound. The surface-active agent or surfactant can include such anionic, cationic and non-ionic agents as have heretofore been generally employed in plant control compositions of similar type. Suitable surface-active agents are set forth, for example in "Detergents and Emulsifiers" 1976 Annual by John W. McCutcheon, Inc.

In general, less than 10% by weight of the surface-active agent will be used in compositions of this invention and ordinarily the amount of surface-active agents will range from 1-5% but may even be less than 1% by weight.

Additional surface-active agents can be added to the formulations to increase the ratio of surfactant:active ingredient up to as high as 5:1 by weight. Such compositions may have a greater effectiveness than can be expected from a consideration of the activity of the components used separately. When used at higher rates, it is preferred that the surfactant be present in the range of one-fifth to five parts surfactant for each one part of active agent.

Water-Soluble Powders

Water-soluble powders are compositions containing the water-soluble active material, an inert solid extender which may or may not be water-soluble, and optionally one or more surfactants to provide rapid wetting and solution. A buffer, which may also function as an extender, can be present to improve formulation stability and to control the pH of the final spray solution.

The classes of extenders suitable for the water-soluble powder formulations of this invention are the natural clays, diatomaceous earth, synthetic mineral fillers derived from silica and silicate, starch, sugar, and inorganic salts. Most preferred fillers for this invention are kaolinites, attapulgite clay, montmorillonite clays, synthetic silicas, synthetic magnesium silicate, calcium sulfate dihydrate, and disodium hydrogen phosphate.

Suitable surfactants for use in such compositions are those listed by J. W. McCutcheon in Detergents and Emulsifiers 1967 Annual. Among the more preferred surfactants are the non-ionic and anionic type, and those most suitable for the preparation of the dry, soluble products of this invention are solid forms of compounds known to the art as wetters and dispersants. Occasionally a liquid, non-ionic compound classified primarily as an emulsifier may serve as both wetter and dispersant.

Most preferred wetting agents are alkylbenzene- and alkylnaphthalene-sulfonates, sulfated fatty alcohols, amines or acid amides, long-chain acid esters of sodium isethionate, esters of sodium sulfosuccinate, sulfated or sulfonated fatty acids esters, petroleum sulfonates, sulfonated vegetable oils, and ditertiary acetylenic glycols. Preferred dispersants are methylcellulose, polyvinyl alcohol, lignin sulfonates, polymeric alkylnaphthalene-sulfonates, sodium naphthalenesulfonate, polymethylene bisnaphthalenesulfonate, and sodium N-methyl-N-(long chain acid) taurates.

Wetting and dispersing agents in these preferred water-soluble compositions of this invention are usually present at concentrations of from about 0.5 weight percent to 5 weight percent. The inert extender then completes the formulation. Where needed, 0.1 weight percent to 1.0 weight percent of the extender may be replaced by a corrosion inhibitor or an anti-foaming agent or both.

Thus, water-soluble formulations of the invention will contain from about 25 to 95 weight percent active material, from 0.5 to 2.0 weight percent wetting agent, from 0.25 to 5.0 weight percent dispersant, and from 4.25 to 74.25 weight percent inert extender, as these terms are described above.

When the water-soluble powder contains a corrosion inhibitor or an anti-foaming agent or both, the corrosion inhibitor will not exceed about 1 percent of the composition, and the anit-foaming agent will not exceed about 0.5 percent by weight of the composition, both replacing equivalent amounts of the inert extender.

Solution Concentrates

The aqueous solution concentrates are prepared by mixing a water-soluble active compound of this invention with water. A portion of the water may be replaced with methanol, ethanol, isopropanol, ethylene gylcol, cellosolve or methyl cellosolve. Surfactants and buffering agents can optionally be present.

These aqueous solution concentrates will contain from 15 to 60% of active ingredient, and from 40 to 85% water or mixture of water and hydroxylated organic solvent. Surfactants, corrosion inhibitors, buffering and antifoam agents may also be included in which case they may replace up to 10% of the solvent system.

Dusts

Dusts are dense powder compositions which are intended for application in dry form, in accordance with the preferred compositions and methods of the invention. Dusts are characterized by their free-flowing and rapid settling properties so that they are not readily windborne to areas where their presence is not desired. They contain primarily an active material and a dense, free-flowing, solid extender.

Their performance is sometimes aided by the inclusion of a wetting agent, and convenience in manufacture frequently demands the inclusion of an inert, adsorptive grinding aid. For the dust compositions of this invention, the inert extender may be either of vegetable or mineral origin, the wetting agent is preferably anionic or non-ionic and suitable adsorptive grinding aids are of mineral origin.

Suitable classes of inert solid extenders for use in the dust compositions are those organic or inorganic powders which possess high bulk density and are very free-flowing. They are also characterized by possessing relatively low surface areas and are poor in liquid adsorption. Suitable classes of grinding aids are natural clays, diatomaceous earths, and synthetic mineral fillers derived from silica or silicate. Among ionic and non-ionic wetting agents, the most suitable are the members of the group known to the art as wetting agents and emulsifiers. Although solid agents are preferred because of ease in incorporation some liquid non-ionic agents are suitable in the dust formulations.

Preferred inert solid extenders for the dusts of this invention are micaceous talcs, pyrophyllite, dense kaolin clays, tobacco dust and ground calcium phosphate rock such as that known as "Phosphodust", a trademark of the American Agricultural Chemical Company.

Preferred grinding aids are attapulgite clay, diatomaceous silica, synthetic fine silica and synthetic calcium and magnesium silicate. Preferred wetting agents are those previously described under water-soluble powder formulations.

The inert solid extenders in the dusts of this invention are usually present in concentrations of from about 30 to 90 weight percent of the total composition. The grinding aid will usually constitute 5 to 50 weight percent of the composition, and the wetting agent will constitute from about 0 to 1.0 weight percent of the composition. Dust compositions can also contain other surfactants such as dispersing agents in concentrations of up to about 0.5 weight percent.

The water-soluble powders described above can also be used in the preparation of dusts. While such water-soluble powders could be used directly in dust form, it is more advantageous to dilute them by blending with the dense dust diluent. In this manner, dispersing agents, corrosion inhibitors, and anti-foam agents may also be found as components of a dust.

Thus, the dust compositions of this invention will comprise about 5 to 20 weight percent active material, 5 to 50 weight percent adsorptive filler, 0 to 1.0 weight percent wetting agent, and about 30 to 90 weight percent dense, free-flowing dust diluent, as these terms are used herein. Such dust formulations can contain, in addition, minor amounts of dispersants, corrosion inhibitors, and anti-foam agents, derived from the water-soluble powders used to make the dusts.

Granules and Pellets

Under some circumstances it may be advantageous to apply the compounds of this invention in the form of granules or pellets. Suitable carriers are natural clays, some pyrophyllites and vermiculites. Wetting agents of the type listed by J.W. McCutcheon in "Detergents and Emulsifiers" 1967 Annual can also be present to aid leaching of the active component.

One method of preparation suitable for both granules and pellets involves blending the active ingredient with clays, water-soluble salts, surfactants and a small amount of water. After pelleting and/or granulating, the formulation is dried prior to use. A second method suitable for the preparation of granules formulation involves spraying a solution of the active material on porous, adsorptive, preformed clay or vermiculite granules. Surfactants listed by McCutcheon can also be included in the spray solution. After drying, the granules are ready for application.

The preferred granules or pellets will contain about 5 to 30 weight percent of active material, about 0 to 5 weight percent wetting agent and about 65 to 95 weight percent inert mineral carrier.

Paints and Dressings

Although the formulations described above can be used to apply the compounds of Formula (1) to cut portions of plants, it is often preferable to incorporate them in conventional tree wound dressings which are commonly used in the trade. Thus, in one step, the cut can be protected and regrowth in the pruned area can be inhibited.

Having high water solubility, the compounds can readily be incorporated in the aqueous phase of conventional asphalt emulsion dressings and water based paints. At the low levels employed (1 – 5%), there is generally little effect on the physical properties of the systems, and commercial materials need not be reformulated. At relatively high levels, the active ingredient, being a salt can cause conventional emulsions to thicken or break. In the former case mere dilution with water is effective to restore physical properties; in the latter case, a salt-tolerant emulsifier must be selected.

As the compounds of Formula (1) have rather low solubility in organic solvents, they must be finely ground and well dispersed to be effective in systems such as solvent-based varnishes and paints. In such systems, the active ingredient must be treated as a pigment would be. Additionally, water must be rigorously excluded, otherwise the active material will not remain well-dispersed.

When packaged as an aerosol, similar considerations apply. The preferred type of formulation is an emulsion with the compound of Formula (1) in the aqueous phase and the film former, solvent and propellant system in the organic phase. Dispersions in organic systems are possible but not preferred because of difficulty in assuring adequate mixing before use, the need to rigorously exclude moisture, and the expense of assuring an adequately fine particle size.

Application

As stated earlier, this invention is founded on the discovery that the compounds of formula (1) are useful for modifying the growth rate of plants. More particularly the compounds of this invention are useful as plant growth retardants. They also affect the flowering and fruit set of numerous plants.

The term plant growth retardant as used in this disclosure is to be understood to mean an agent which when applied to a plant or its environs will slow the growth of the plant without killing or causing extensive injury to said plant. This also includes a delaying response on bud sprouting or prolonging of the dormancy period.

The compounds of this invention can be used to retard bud break and the growth of woody vegetation. The compounds of this invention can also be used to control the growth of turf and other herbaceous vegetations.

The compounds of this invention can be applied as foliar sprays or as soil applications to retard the growth rate of such plants or to affect flowering and fruit set.

Preferably, the compounds of this invention are applied as a foliar spray to the point of runoff although lower-volume application may also be effective.

It is preferred that the application be made a short time prior to the period when maximum plant growth is anticipated, but application can also be made during the dormant stage or just after the plants have been trimmed. Or if flowering and fruit set are to be modified, the treatment is applied before, during, or shortly after flowering.

To prevent bud break it is preferred that the application be made at the time the buds for the next year are being developed. For most plants this is from July to a few weeks before leaf-fall.

It will be recognized that the rate of application is dependent upon the species to be treated and the results desired. In general, rates of from 0.25 to 20 kilograms per hectare are used although higher or lower rates can achieve the desired effect in some instances.

The following examples are presented to further illustrate the formulation and application of the compounds of this invention. Parts and percentages in the following examples are by weight unless otherwise indicated.

EXAMPLE 81

A dust having the following formula is prepared.

| | |
|---|---|
| Ammonium allyl carbamoylphosphonate | 5.0% |
| Talc | 64.0% |
| Attapulgite | 30.0% |
| Sodium benzenesulfonate | 1.0% |

The active component is ground with the minor diluent and the surfactant to pass a 0.149 mm. screen. This material is then blended with a major diluent to form a dust composition.

It will be understood that the other compounds of this invention can also be formulated in a like manner.

The dust formulation of Example 81 is applied, using a helicopter, at a rate of 100 kilograms per hectare to an area under an electric power line in which the brush and trees have been freshly trimmed in spring at the time when the leaves on most of the plants are just fully expanded.

The application is made in the early morning when the foliage is wet with dew or just after a rain. This treatment retards the growth of a large number of species along the right-of-way including the following species: red maple (*Acer rubrum*), black willow (*Salix nigra*), hawthorn (*Crataegus spp.*), sweet gum (*Liquidamber styraciflua*) and yellow poplar (*Liriodendron tulipifera*).

EXAMPLE 82

A water-soluble powder of the following formula is prepared.

| | |
|---|---|
| Ammonium allyl carbamoylphosphonate | 95.0% |
| Synthetic silica | 3.5% |
| Disodium hydrogen phosphate | 1.0% |
| Dioctylsodium sulfosuccinate | 0.5% |

The above ingredients are mixed and then ground to pass a 0.42 mm. screen. The resulting formulation is water-soluble powder, with the exception of the synthetic silica conditioning agent.

The following compounds of this invention can also be formulated in like manner.

Ammonium 2-chloroethyl carbamoylphosphonate
Ammonium methyl carbamoylphosphonate
Sodium phenyl carbamoylphosphonate
Hemicalcium benzyl carbamoylphosphonate
Hemibarium ethyl carbamoylphosphonate
Ammonium 2,3-dibromopropyl carbamoylphosphonate
Diethylammonium ethyl carbamoylphosphonate
Ammonium hexyl carbamoylphosphonate Four kilograms of the water-soluble powder formulation of Example 82 is dissolved in 200 liters of water and 0.5% of a non-phytotoxic wetting agent is added. This solution is sprayed on one hectare of freshly trimmed Norway maple (*Acer plantanoides*) growing along struts under a power line. This treatment greatly reduces the rate of growth of the trees and extends the time interval between trimmings. The trees are not significantly injured by the treatment.

The water-soluble powder of Example 82 can be dissolved in water at the rate of 2000 p.p.m. of active ingredient and applied to one acre of Virginia bunch peanuts at the time they are beginning to flower. The treatment prevents excessive vegetative growth and promotes flowering and fruit set of the treated plants. As a result of the treatment the plants are easier to harvest and dry and more high quality nuts are harvested.

EXAMPLE 83

| | |
|---|---|
| Ammonium ethyl carbamoylphosphonate | 90% |
| Silica aerogel | 4% |
| Sugar | 6% |

The ingredients are combined, blended, crushed through a U.S.S. No. 20 sieve (0.84 mm. openings) and reblended.

In mid-September, active ingredient formulated as described above was dissolved in water containing 0.2% sorbitan monolaurate and applied to the foliage of red maple (*Acer rubrum*), sweet gum (*Liquidambar styraciflua*) and green briar (*Smilax spp.*) at the rate of 3 kg/ha in 800 l. of water. The treatment had no apparent effect on the plants for the remainder of the season. However, the next July the treated plants had developed almost no leaves. What buds that had broken had produced only minute red-tinged leaves. Except for some tips, the bare branches were still alive. The floor beneath the treated brush was green with herbaceous vegetation.

EXAMPLE 84

A wettable powder of the following formula is prepared.

| | |
|---|---|
| Hemibarium benzyl carbamoyl-phosphonate | 50.0% |
| Montmorrilonite | 43.0% |
| Synthetic silica | 4.0% |
| Disodium hydrogen phosphate | 1.0% |
| Sodium alkylnaphthalenesulfonate | 1.0% |
| Sodium lignin sulfonate | 1.0% |

The above ingredients are mixed and then ground to pass a 0.25 mm. screen. The active ingredient in the above formulation dissolves when the composition is added to water.

Twenty kilograms of the formulation of Example 84 is added to 400 liters of water and agitated until the active ingredient dissolves. This solution is then sprayed on one hectare of newly trimmed hedgerow in the spring after the leaves have expanded. This treatment greatly reduces the growth of plants growing in the hedgerow such as osage orange (*Maclura pomifera*), but does not seriously injure them. The hedgerow is thus kept neat with a minimum of labor expended for trimming it.

EXAMPLE 85

A solution of the following formula is prepared.

| | |
|---|---|
| Ammonium ethyl carbamoylphosphonate | 24.0% |
| Disodium hydrogen phosphonate | 1.0% |
| Sodium laurylsulfate | 0.5% |
| Water | 74.5% |

The above components are blended to form a homogeneous solution.

The following compounds can be formulated in like manner.

Benzyltrimethylammonium benzyl N,N-dimethylcarbamoylphosphonate
Trimethylammonium ethyl N-methylcarbamoylphosphonate
Methylammonium isopropyl morpholinocarbonylphosphonate
Triethylammonium ethyl carbamoylphosphonate Ten kilograms of the solution prepared in Example 85 are added to 200 liters of water and applied with a fixed boom sprayer to one hectare of Kentucky bluegrass (*Poa pratensis*) turf growing along a highway in early June. This treatment greatly reduces the rate of growth of the bluegrass for a period of four to eight weeks and the mowing required to maintain the area in an attractive condition is reduced.

EXAMPLE 86

A solution of the following formula is prepared.

| | |
|---|---|
| Allylammonium allyl N,N-dimethylcarbamoyl-phosphonate | 24.0% |
| Trimethylnonylpolyethyleneglycol ether | 1.0% |
| Water | 20.0% |
| Eythylene Glycol | 55.0% |

The above components are blended to form a homogeneous solution.

The following components can be formulated in like manner.

Ethanolammonium methallyl hexahydroazepinocarbonylphosphonate
Dodecyltrimethylammonium butyl N-methylcarbamoylphosphonate
Ammonium n-hexyl carbamoylphosphonate Six kilograms of the formulation of Example 86 are added to 400 liters of water containing 0.5% Tween 20 (*Polyoxyethylenesorbitan monolaurate*). This solution is sprayed to runoff on a freshly trimmed privet (*Ligustrum ovalifolium*) in May. The treatment greatly reduces the growth of the hedge. Little labor is required to keep it attractive all season.

A solution containing 227 gms. of active ingredient formulated as above is sprayed on an area of red delicious apple trees about two weeks after petal fall. This treatment prevents the "June drop" and gives a higher yield of apples per acre than that from a similar untreated acre of trees. It also reduces the growth of spurious shoots known as "water sprouts" and ameliorates the tendency to biannual bearing which is strong in this variety.

EXAMPLE 87

The following formulation is prepared.

| | |
|---|---|
| Ammonium methyl carbamoylphosphonate | 25.0% |
| Sodium lauryl sulfate | 50.0% |
| Magnesium silicate | 10.0% |
| Kaolinite | 15.0% |

The above components are blended, micropulverized to pass a 0.30 mm. screen and reblended.

The following compounds can be formulated in like manner.

Morpholinium ethyl carbamoylphosphonate
Sodium phenyl carbamoylphosphonate
hemicalcium benzyl carbamoylphosphonate Five kilograms of the formulation of Example 87 are suspended in 100 liters of water and then sprayed to runoff on freshly trimmed trees and brush along the edge of a power line right-of-way. This treatment greatly reduces the growth of the trees and shrubs without permanent injury to them and they are prevented from growing over into the power line. The vegetation on the right-of-way is controlled by applying herbicides. This treatment reduces the labor required to maintain the line.

EXAMPLE 88

An aqueous concentrate solution is prepared which contains the following ingredients:

| | |
|---|---|
| ammonium ethyl carbamoylphosphonate | 24.0% |
| N-dimethylaminosuccinamic acid | 12.0% |
| water | 32.0% |
| methanol | 32.0% |

The above ingredients are stirred together with slight warming until a homogeneous solution results.

A water solution of the formulation of Example 88 is prepared to contain 600 p.p.m. total active ingredient. This solution is sprayed on McIntosh apples to run-off in early September. The treatment prevents coloration in the apples and prevents premature fall before the apples are harvested.

EXAMPLE 89

| Ammonium ethyl carbamoylphosphonate | 41.5% |
|---|---|
| Water | 58.5% |

The ingredients are combined and stirred to produce a solution containing approximately 4 pounds active ingredient per gallon (480 g. per liter). After filtration through a bed of diatomaceous earth, the product is packed in glass or plastic containers until use.

In September, oaks (*Quercus spp.*), hickory (*Carya spp.*) and Loblolly pine (*Pinus taeda*) were treated with a foliar spray of the above formulation at the rate of 6 kg/ha in 800 liters of water. The treated plants showed no response that fall but next spring the deciduous species failed to develop new leaves and the pine did not develop new shoots. The treatment had prevented the new buds from breaking in the spring although plant stems and limbs were observed to be alive when examined closely.

EXAMPLE 90

The following wettable powder is prepared:

| ammonium ethyl carbamoylphosphonate | 30.0% |
|---|---|
| maleic hydrazide | 20.0% |
| synthetic silica | 2.5% |
| montmorillonite | 45.0% |
| sodium alkylnaphthalene sulfonate | 2.0% |
| partially desulfonated sodium lignin sulfonate | 0.5% |

The above ingredients are blended, micropulverized to a particle size essentially below 50 microns and reblended.

The wettable powder of Example 90 is suspended in water at the rate of 4,000 p.p.m. of active ingredient and sprayed on an area of mixed brush under a power line. The application is made in mid-May just after the brush has been trimmed back to keep it away from under the power line. The solution is sprayed to run-off on the lower two-thirds of the trees which were not cut. This treatment effectively retards the growth of the trimmed vegetation for the next growing season as well as the one in which the vegetation is treated.

The formulation of Example 90 is suspended in water at the rate of 1,000 p.p.m. of active ingredient and sprayed to the point of run-off on single trees located at random throughout orchards of apple, peach and cherry varieties. The treatments are applied while the trees are still in the dormant stage. During an early spring warm period the trees in these orchards begin to break dormancy and buds sprout. The treated trees, on the other hand, remain dormant and do not sprout nor flower while there is danger of frost. In this manner, a more reliable yield is assured.

EXAMPLE 91

The following aerosol preparation is prepared:

| | | |
|---|---|---|
| A | ammonium ethyl carbamoylphosphonate | 1.0% |
| | water | 29.0% |
| B | asphalt | 20.0% |
| | xylene | 25.0% |
| | polyglycerol stearate | 5.0% |
| C | dichloro difluoromethane | 20.0% |

The predissolved aqueous phase (A), comprising active ingredient in water, is combined with the organic phase (B), comprising a solution of asphalt, emulsifier, and xylene, with agitation. To this is added, under pressure in an aerosol dispenser, the propellant C.

Trees under a power line are trimmed back in early May to prevent them growing into the lines. The cut ends are treated with the wound dressing described above. The treatment reduces the break of lateral buds and retards the rate of growth of those that do break. In addition, the treatment causes overall retardation in the rate of growth of the treated plants. This lengthens the time between trimmings, reducing the cost of maintaining the power line. Trees treated include sweetgum (*Liquidambar styraciflua L.*), black willow (*Salix nigra Marsh.*), apple (*Malus sp. Mill.*), and red maple (*Acer rubrum L.*).

EXAMPLE 92

The following asphalt emulsion is prepared:

| ammonium ethyl carbamoylphosphonate | 4.0% |
|---|---|
| sodium oleate | 2.0% |
| water | 47.0% |
| asphalt | 47.0% |

The active compound, sodium oleate and water are combined and heated to 90° C. In a high shear mixer, molten asphalt is added. The suspension is cooled and packaged.

This emulsion containing 4% ethyl carbamoylphosphonate is applied as a wound dressing in late Spring following conventional pruning on red maple (*Acer rubrum L.*), red oak (*Quercus borealis Michx.*), paper birch (*Betula papyrifera Marsh.*), and sugar maple (*Acer saccharum Marsh.*), growing under a power line. The treatment retards the breaking of lateral buds and the rate of growth of laterals. This reduces the future trmming necessary to maintain the area.

I claim:

1. A compound of the formula $$R_1-O-\underset{\underset{OM}{|}}{\overset{\overset{O}{\|}}{P}}-\overset{\overset{O}{\|}}{C}-N\overset{R_2}{\underset{R_3}{\diagdown}}$$

where
$R_1$ is alkyl of one through six carbon atoms, chloroalkyl of one through six carbon atoms containing up to three chlorine atoms, bromoalkyl of one through six carbon atoms, containing up to three bromine atoms, alkoxy alkyl of three through seven carbon atoms, alkenyl of two through six carbon atoms, alkynyl of three through four carbon atoms, phenyl or benzyl;
$R_2$ is hydrogen or methyl;
$R_3$ is hydrogen or methyl;
M is zinc or $$\overset{R_6}{\underset{R_7}{\diagdown}}\overset{+}{N}\overset{R_8}{\underset{R_9}{\diagup}}$$

where $R_6$ and $R_7$ can be taken together to form a ring that is $-(CH_2)_2-O-(CH_2)_2-$ or $-(CH_2)_n-$ where $n$ is 2-6 and $R_8$ and $R_9$ are hydrogen.

* * * * *